United States Patent
Girgis et al.

(10) Patent No.: US 10,005,057 B1
(45) Date of Patent: Jun. 26, 2018

(54) SEGMENTED REACTOR FOR HOMOGENEOUS REGENERATION OF SPENT IONIC LIQUID

(71) Applicant: Chevron U.S.A. Inc., San Ramon, CA (US)

(72) Inventors: Michael John Girgis, Richmond, CA (US); Huping Luo, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days. days.

(21) Appl. No.: 15/715,235

(22) Filed: Sep. 26, 2017

(51) Int. Cl.
| | |
|---|---|
| B01J 10/00 | (2006.01) |
| B01J 31/40 | (2006.01) |
| C07D 213/20 | (2006.01) |
| B01J 31/02 | (2006.01) |
| B01J 38/10 | (2006.01) |

(52) U.S. Cl.
CPC ......... B01J 10/002 (2013.01); B01J 31/0284 (2013.01); B01J 31/0298 (2013.01); B01J 31/4015 (2013.01); B01J 38/10 (2013.01); C07D 213/20 (2013.01)

(58) Field of Classification Search
CPC ...... B01J 10/002; B01J 31/0284; B01J 38/10; B01J 31/4015; B01J 31/0298; C07D 213/20
See application file for complete search history.

(56) References Cited

U.S. PATENT DOCUMENTS

| | | | |
|---|---|---|---|
| 2,910,513 A | 10/1958 | Ridgway et al. | |
| 7,651,970 B2 | 1/2010 | Elomari et al. | |
| 7,674,739 B2 | 3/2010 | Elomari et al. | |
| 7,691,771 B2 | 4/2010 | Harris et al. | |
| 7,732,363 B2 | 6/2010 | Elomari et al. | |
| 8,747,656 B2 | 6/2014 | Tonkovich et al. | |
| 9,802,186 B2 * | 10/2017 | Luo ..................... | B01J 31/40 |
| 2007/0249486 A1 | 10/2007 | Elomari | |
| 2014/0039230 A1 | 2/2014 | Timken | |
| 2017/0216827 A1 * | 8/2017 | Girgis ................. | B01J 31/40 |

FOREIGN PATENT DOCUMENTS

| | | |
|---|---|---|
| CN | 104174275 A | 12/2014 |
| GB | 1416194 | 12/1975 |

OTHER PUBLICATIONS

Pines, H., The Chemistry of Catalytic Hydrocarbon Conversions, Wiley, 1981, p. 39ff.

(Continued)

*Primary Examiner* — Randy Boyer
*Assistant Examiner* — Juan C Valencia
(74) *Attorney, Agent, or Firm* — Susan M. Abernathy

(57) ABSTRACT

We provide a segmented reactor for regenerating a spent acidic ionic liquid via a hydrogenation reaction and hydrocracking, comprising: no solid hydrogenation catalyst; a gas inlet on one side for feeding a gas feed comprising a hydrogen; a liquid inlet on an opposite side for feeding a spent acidic ionic liquid; partitions along an axis of the reactor that create segments, wherein each segment functions as a bubble column reactor; and an outlet from which a regenerated acidic ionic liquid flows out of the segmented reactor.

17 Claims, 4 Drawing Sheets

(56) References Cited

OTHER PUBLICATIONS

Pines, H., Chemtech, Saga of a Discovery, Alkylation 1982, p. 150.
Miron, S. and Lee, R.J., Molecular Structure of Conjuct Polymers, n J. Chem. Eng. Data, 1963, p. 150.
Ingred M. Angulo et al., Journal of Molecular Catalysis A: Chemical 202 (2003) 97-106.
U.S. Appl. No. 14/481,145, filed Sep. 9, 2014.
Gadalla, A.M., T.C. Chan, and R.G. Anthony, Int J. Chem. Kinet 15,759 (1983).
Sano, T., O. Kiyomi, H. Hagiwara, H. Takaya, J. Shoji, and K. Matsuzaki, J. Mol Catal, 40, 113 (1987).
Garwood, William E. and Dwyer Francis G., Shape Selective Catalysis in Industrial Applications, 146-147.

\* cited by examiner

SEGMENTED REACTOR FOR HOMOGENEOUS REGENERATION OF SPENT IONIC LIQUID

TECHNICAL FIELD

This application is directed to a segmented reactor having no solid hydrogenation catalyst, which is used for regenerating a spent acidic ionic liquid.

BACKGROUND

Improved processes are needed for regenerating spent acidic ionic liquids. Earlier processes have required reactors comprising significant quantities of hydrogenation catalysts to perform the hydro-regeneration. Hydrogenation catalysts that were used in the earlier processes and equipment needed to be periodically replaced and/or regenerated, and they were costly to purchase, handle, and dispose of.

SUMMARY

This application provides a segmented reactor for regenerating a spent acidic ionic liquid via a hydrogenation and a hydrocracking, comprising: no solid hydrogenation catalyst; a gas inlet on a first side of the segmented reactor for feeding a gas feed comprising a hydrogen; a liquid inlet on an opposing side (opposite of the first side) of the segmented reactor for feeding a spent acidic ionic liquid; partitions along an axis of the segmented reactor that create segments, wherein each segment functions as a bubble column reactor; and an outlet from which a regenerated acidic ionic liquid flows out of the segmented reactor.

The present invention may suitably comprise, consist of, or consist essentially of, the elements in the claims, as described herein.

GLOSSARY

Figure 1:
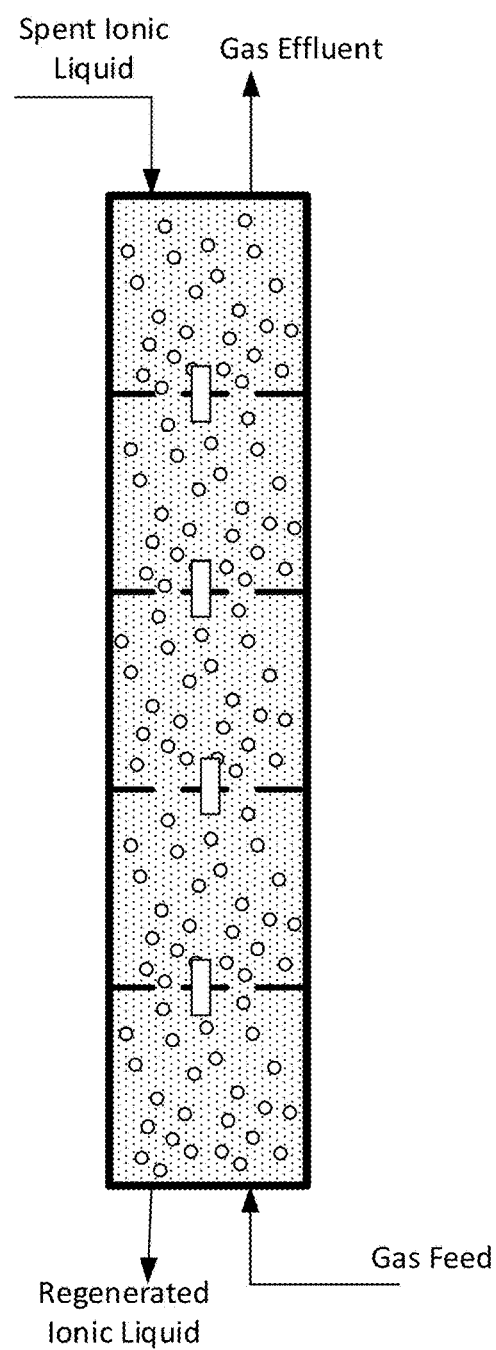
FIG. 1 is a drawing of one embodiment of a segmented reactor for regenerating a spent acidic ionic liquid having a gas inlet on one side and a liquid inlet on an opposing side.

"Segmented reactor" refers to a reactor that is composed of segments or sections.

"Acidic ionic liquid" refers to a material consisting entirely of ions, that can donate a proton or accept an electron pair in reactions, and that is liquid below 100° C.

"Spent" refers to a less active catalytic material that has been contaminated during use, typically with a conjunct polymer.

"Bubble column reactor" refers to an apparatus used for gas-liquid reactions in which the gas, in the form of bubbles, comes in contact with the liquid while moving in the liquid column and providing a driving force for mixing. In a bubble column reactor the liquid is the continuous phase and the gas is the dispersed phase.

"Addition" refers to a purposeful step of adding a different material, e.g., a hydrogenation catalyst, to a vessel or reactor used for the contacting.

"Hydrogenation" refers to a chemical reaction between molecular hydrogen ($H_2$) and another compound or element to reduce or saturate organic compounds. For example, hydrogenation reduces double and triple bonds in hydrocarbons.

"Hydrogenation catalyst" in the context of this disclosure refers to a solid metal-containing catalytic material that performs hydrogenation of organic compounds.

"Periodic Table" refers to the version of the IUPAC Periodic Table of the Elements dated Jun. 22, 2007, and the numbering scheme for the Periodic Table Groups is as described in Chemical And Engineering News, 63(5), 27 (1985).

"Conjunct polymer" refers to poly-unsaturated cyclic, polycyclic, and acyclic molecules formed by concurrent acid-catalyzed reactions including, among others, polymerization, alkylation, cyclization, and hydride transfer reactions. Conjunct polymers contain double and conjugated double bonds in intricate structures containing a combination of cyclic and acyclic skeletons. Examples of conjunct polymers are described by Miron et al. (Journal of Chemical And Engineering Data, 1963) and Pines (Pines, H., The Chemistry of Catalytic Hydrocarbon Conversions, Wiley, 1981, p. 39ff).

"Hydrocracking" refers to a process in which hydrogenation and dehydrogenation accompanies the cracking/fragmentation of hydrocarbons, e.g., converting heavier hydrocarbons into lighter hydrocarbons, or converting aromatics and/or cycloparaffins (naphthenes) into non-cyclic branched paraffins.

"Noble metal" refers to a metal that is resistant to corrosion and oxidation in moist air (unlike most base metals). Examples of noble metals are ruthenium, rhodium, palladium, silver, osmium, iridium, platinum, and gold.

"Plug flow reactor" refers to a reactor with one or more continuous flowing systems of cylindrical geometry.

"Bubble cap" refers to a device (such as a metal cup with notches or slots around the edge) that is inverted over a hole or a perforation, in a plate in a segmented reactor for effecting contact of a gas rising from the plate below and liquid already on the plate.

DETAILED DESCRIPTION

Hydrogenation is known to be an effective method used to regenerate spent acidic ionic liquids, but the processes known previously all required the addition of a solid hydrogenation catalyst to reduce a conjunct polymer in the spent acidic ionic liquid.

Segmented Reactor

The segmented reactor comprises no solid hydrogenation catalyst and provides no addition of a solid hydrogenation catalyst. The segmented reactor comprises a gas inlet on a first side of the segmented reactor for feeding a gas feed comprising a hydrogen, a liquid inlet on an opposing side (opposite to the first side) of the segmented reactor for feeding a spent acidic ionic liquid, and partitions along an axis of the reactor that create segments, wherein each segment functions as a bubble column reactor. Additionally, the segmented reactor comprises an outlet from which a regenerated acidic ionic liquid flows out of the reactor. In one embodiment, the number of segments in the segmented reactor can vary from two to twenty.

The axis of the segmented reactor can be in any direction, as long as there is sufficient mixing and the process conditions are conducive to the regeneration. In one embodiment, the axis is vertical.

In one embodiment, a placement of the gas inlet and the liquid inlet create a counter-current flow within the segmented reactor. One example of this configuration of the segmented reactor is shown in FIG. 1. A counter-current flow within the segmented reactor can be advantageous, by causing contacting of an effluent ionic liquid stream within the segmented reactor with a fresh gas feed with a higher hydrogen concentration, which provides more conversion and reduction of conjunct polymers in the spent acidic ionic liquid.

Referring to FIG. 1, the outlet that elutes the regenerated acidic ionic liquid is at a bottom of the segmented reactor and a gas outlet at a top of the segmented reactor elutes a gas effluent. In this figure, the gas inlet is at the bottom of the segmented reactor and the liquid inlet is at the top of the segmented reactor.

The various inlets and outlets are placed strategically on the segmented reactor to provide sufficient mixing and process conditions that are conducive to the regeneration. In one embodiment, the gas inlet is on a lower portion of one or more segments in the reactor. In one embodiment, the outlet is on an upper portion of one or more segments. In one embodiment, the gas inlet and the liquid inlet can be at the bottom of the segmented reactor, on opposite sides from each other, and the outlet is above the bottom of the segmented reactor. In one embodiment, the gas feed and the spent acidic ionic liquid flow directionally through the segmented reactor, and do not flow back from a subsequent segment to an earlier segment in the segmented reactor. In one embodiment, the gas feed flows upwardly through the segmented reactor, and does not flow back from an upper segment to a lower segment in the segmented reactor.

In an embodiment, one purpose of the segments in the segmented reactor is to induce back mixing of a liquid phase comprising the spent acidic ionic liquid. The gas feed comprising hydrogen flows continuously through the reactor such that the reactor operates as a plug flow reactor. In one embodiment, the partitions in the segmented reactor provide an overall plug flow pattern in the reactor such that both the spent acidic ionic liquid and the gas feed flow continuously through the reactor without back mixing into an earlier segment.

In one embodiment, the gas inlet is designed to introduce a gas feed stream uniformly into the cross-section of a reactor column to enable an optimum gas exchange with the spent acidic ionic liquid. In one embodiment, the gas inlet that feeds the gas feed comprising the hydrogen is a perforated plate, or a plate with many small holes drilled into it, which allows gas bubbles to flow easily through the perforations. In one embodiment, the gas inlet used for feeding the gas feed comprising the hydrogen is a gas sparger. In one embodiment, the gas sparger distributes the gas feed stream via many cross-linked pipes arranged in such a way that it uniformly injects gas bubbles from many small holes drilled on the cross-linked pipes into an entire flow cross-section of the segmented reactor. In another embodiment, the gas inlet for feeding the gas feed comprising the hydrogen is a porous medium. Porous media can introduce gases into liquids through many tiny pores, creating bubbles far smaller and more numerous than with typical sparging methods. In one embodiment, the gas inlet can produce gas bubbles with a mean diameter less than 20 mm, such as from 0.1 mm to 10 mm.

In one embodiment, the gas feed rate can be adjusted and controlled. The gas feed rate should be adequate to provide sufficient mixing and mass transfer between the gas bubbles and the liquid phase in the segmented reactor. In one embodiment, the gas feed rate and a column diameter of the segmented reactor are designed to provide a superficial gas velocity (defined as the gas flow rate under the reactor conditions divided by the cross-sectional area of the reactor column) of 0.01 cm/s to 5 cm/s.

The liquid inlet for feeding the spent acidic ionic liquid is designed to give adequate flow and mixing with the gas feed comprising hydrogen. Examples of suitable liquid inlets include tubing, piping, drilled piping, nozzles, nipples, and others. In one embodiment the mass flow ratio of a liquid feed comprising the spent acidic ionic liquid to a gas feed in the segmented reactor is 1-100. In another embodiment, the mass flow ratio of a liquid feed to a gas feed in the segmented reactor is 10-50.

In one embodiment the segmented reactor additionally comprises a diluent inlet for introducing a hydrocarbon solvent. In another embodiment, the liquid inlet for feeding a spent acidic ionic liquid is designed to feed a liquid feed that is a mixture of the spent acidic ionic liquid and a hydrocarbon solvent. Some examples of hydrocarbon solvents that can be used in the segmented reactor include normal paraffins, isobutane, alkylate gasoline, isomerized olefin, and mixtures thereof. The use of certain types of hydrocarbon extraction solvents during hydro-regeneration of acidic ionic liquids is described in US Pat. Pub. No. US20140039231A1. In one embodiment, the hydrocarbon solvent is selected and added in an amount to the liquid feed to reduce corrosion in the segmented reactor.

The segmented reactor comprises partitions along an axis of the segmented reactor that create segments within the reactor. Examples of partitions include screens, perforated plates, particulate filtration media, sieve trays, and combinations thereof. In one embodiment, the partitions are perforated plates. In one embodiment, the partitions comprise openings and the openings provide high gas-liquid velocity. For example, the high gas-liquid velocity in the segmented reactor can be from 1 to 100 cm/s.

In one embodiment, the openings in the partitions in the segmented reactor allow gas to flow only upward from a lower segment to an upper segment, such that the overall segmented reactor operates as a plug flow reactor. A plug flow reactor (PFR) is a type of chemical reactor where the influent is pumped into the direction of flow within the length of the reactor. Chemical reactions occur along the length of the PFR and the reaction rate varies along the reactor axis.

In one embodiment, the partitions along the axis of the segmented reactor distribute gas bubbles evenly across the cross-section of the reactor column within each segment in the segmented reactor. In one embodiment, the partitions along the axis of the segmented reactor are the only internals in the segmented reactor.

In one embodiment, the partitions along the axis of the segmented reactor have openings that are at least 0.1 cm in diameter, or big enough to avoid being plugged up by solid impurities in the reactor system. In another embodiment, the partitions along the axis of the segmented reactor have openings that are at most 5 cm in diameter, or small enough, to create a high enough pressure drop across the partition to prevent gas and/or liquid flow back from an upper segment to a lower segment. In one embodiment, the partitions have openings that are 0.5 to 2.5 cm in diameter. In one embodiment, the partitions comprise perforated plates having many holes of diameter 0.5 to 2.5 cm. The number of holes in the partitions can vary between the different partitions or be the same in one or more of the partitions. In one embodiment, the number of openings in the partitions can vary from 3-1000.

Figure 2:
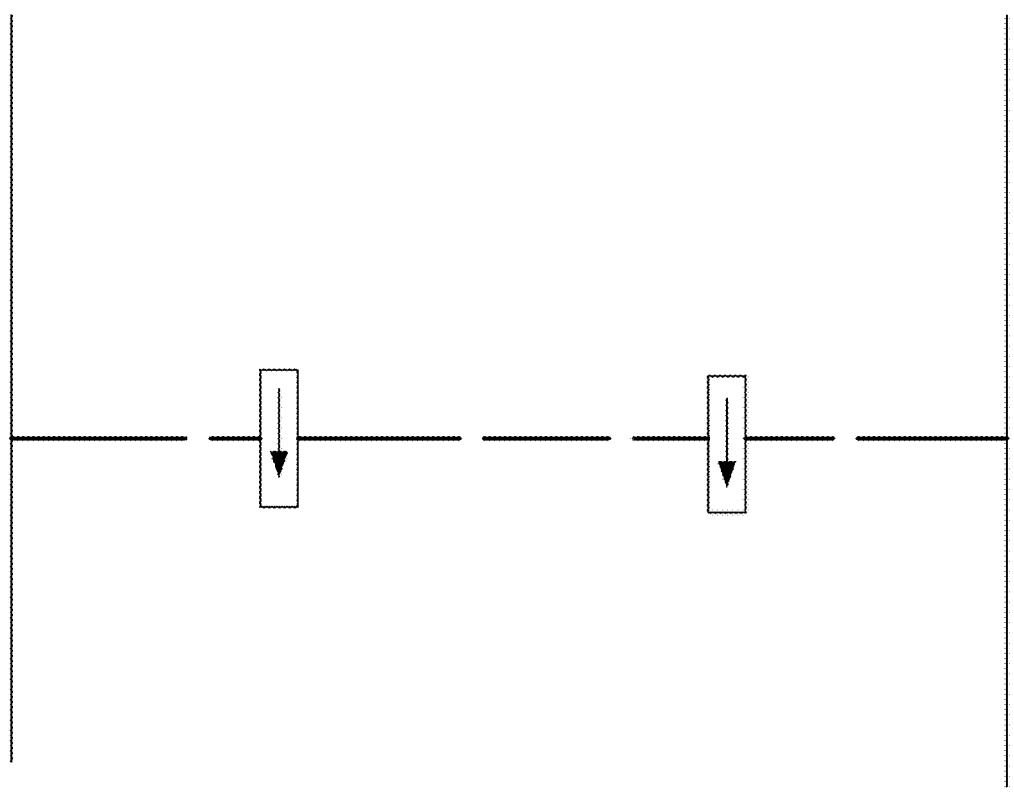
FIG. 2 is a drawing of one example of a perforated plate within the segmented reactor that is equipped with down flow pipes.

In one embodiment, to improve contact between the gas feed and the spent acidic ionic liquid in the segmented reactor operating under a counter-current flow, the partitions can comprise perforated plates equipped with down flow pipes. This embodiment is illustrated in FIG. 2. The down flow pipes can provide improved liquid flow downward from an upper segment to a lower segment in the segmented reactor. In FIG. 2, the partition additionally comprises orifices that conduct gas bubbles upwardly through the segmented reactor. As shown in FIG. 2, gas bubbles move up from one segment to another via orifices in the perforated plate, while liquids flow down through the down flow pipes.

Figure 3:
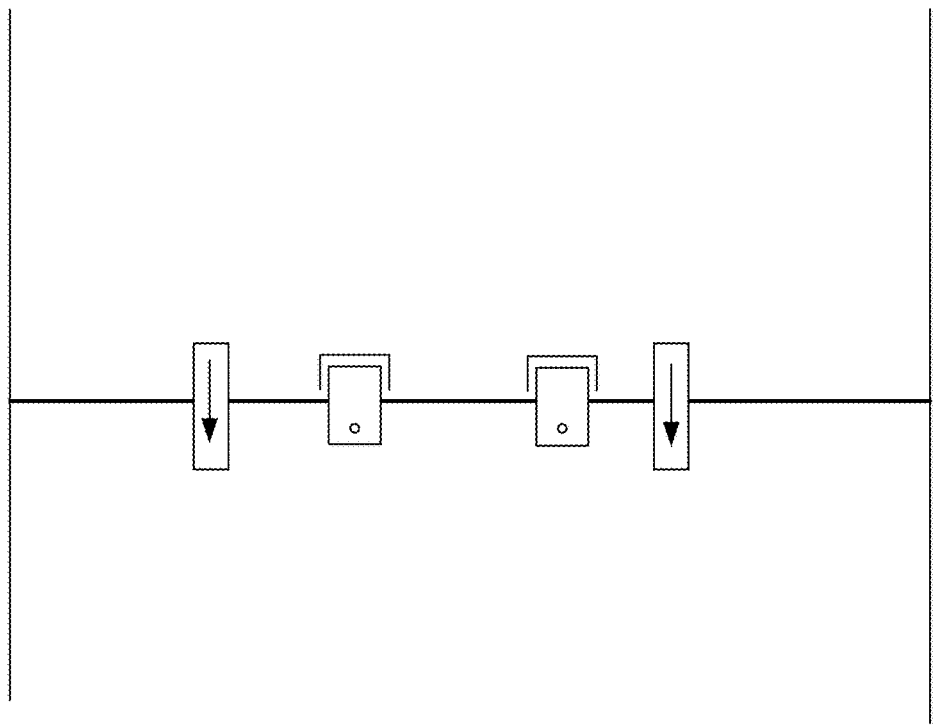
FIG. 3 is a drawing of one example of a segmented reactor equipped with a partition having bubble caps and down flow pipes.

In another embodiment, the partitions in the segmented reactor can comprise one or more plates that are equipped with at least one down flow pipe and at least one gas/liquid contact device. Examples of gas/liquid contact devices that could be used include bubble cap trays and valve trays. This embodiment is illustrated in FIG. 3. FIG. 3 demonstrates a segmented reactor with a partition comprising down flow pipes and bubble caps. Gas bubbles in this embodiment move up from one segment to another via the bubble caps and liquids flow down through the down flow pipes.

In one embodiment, the partitions comprise a valve tray, a bubble cap tray, or a combination thereof. In a valve tray, perforations in the valve tray are covered by lift-able caps. Gas flows lift the caps, thus self-creating a flow area for the passage of gas. The lifting cap directs the gas to flow horizontally into the liquid, thus providing better mixing than is possible in sieve trays or simple perforated plates. A bubble cap tray has a riser or a chimney fitted over each hole or perforation in the tray, and a cap that covers the riser or the chimney. The cap is mounted so that there is a space between the riser and the cap to allow the passage of gas. The gas in the bubble cap tray rises through the riser or the chimney and is directed downward by the cap, eventually discharging through slots in the cap, and finally bubbling through the liquid on the tray.

Figure 4:
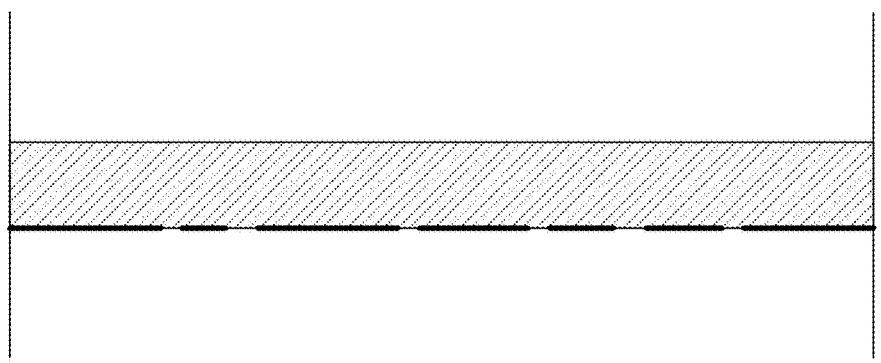
FIG. 4 is a drawing of one example of a segmented reactor equipped with a perforated plate having a layer of solids above the perforated plate.

In one embodiment, the segmented reactor comprises partitions having a layer of one or more solids that create a flow resistance for gas and liquid flows within the segmented reactor. For example, the segmented reactor can comprise partitions that are perforated plates or sieve trays having a layer of one or more solids. The flow resistance created by the layer of the one or more solids can prevent back-mixing of gas and liquid flows from adjacent segments in the segmented reactor. This embodiment is shown in FIG. 4. Any solids that serve this purpose can be used. Some examples include inert ceramic balls, Crystaphase CatTrap® internal particulate filter media, alumina, and mixtures thereof.

In one embodiment, particulate filter media having no hydrogenation activity can be added to the top of one or more of the partitions for improving dispersion and/or adsorbing any contaminants from the spent acidic ionic liquid. One example of a suitable particulate filter medium is a Crystaphase CatTrap® internal particulate filter media. In one embodiment, the internal particulate filter medium comprises a reticulated ceramic which comes in large discs (1.5" to 2" diameter). These discs can have the ability to filter and store particles inside the discs, while the large dimensions of the discs keep the material from filtering externally. Because the large external pathways stay open, there is no pressure drop build up as the material filters. Apparatuses including appropriately designed internal particulate filter systems can require less space than traditional grading systems and can provide the additional benefit of no pressure drop over the length of the segmented reactor. In a further embodiment, a layer of 2.5 cm to 15 cm thick Crystaphase CatTrap® or similar internal particulate filter media can be added to the partition of one or more, or all, of the segments in the segmented reactor. In one embodiment, the particulate filter medium can have a pore size from 0.001 to 0.25 cm, or greater than 0.005 cm.

In one embodiment, the partitions are inserted into a conventional bubble column reactor. Conventional bubble column reactors are those previously designed or constructed for known chemical reactions, such as wet oxidation or algae bio-reactions. Conventional bubble column reactors have vertically arranged cylindrical columns where the gas inlet is at the bottom of the reactor and the liquid can flow through the reactor in parallel flow or counter-current to the flow of the gas in the reactor.

In one embodiment, the segmented reactor additionally comprises a vent at the top of the segmented reactor that collects paraffinic light gases that are formed during a contacting of the hydrogen and the spent acidic ionic liquid. Examples of paraffinic light gases include methane, ethane, propane, butanes, and pentanes. These light gases can be entirely non-olefinic, and may comprise $C_2$-$C_4$ alkanes, such as ethane, propane, i-butane, and n-butane. In one embodiment, at least a portion of the paraffinic light gases are formed by the hydrocracking in the segmented reactor.

In one embodiment, the segmented reactor additionally comprises a level control valve or a lateral effluent outlet, which maintains a steady level of a liquid in the segmented reactor. One or more guard bed vessels containing adsorbent material with appropriate pore size can be added before the segmented reactor to minimize contaminants going into the segmented reactor from the gas feed, the spent acidic ionic liquid, or from both.

In one embodiment, the segmented reactor is sized, designed, or positioned within a process unit, such that the temperature is maintained below 380° C. In one embodiment, the temperature in the segmented reactor is maintained from 100° C. to 350° C. to provide optimal conditions for producing the regenerated acidic ionic liquid. For example, the segmented reactor can comprise a temperature controller than maintains the temperature in the segmented reactor from 100° C. to 350° C. The relatively low operating temperature in the segmented reactor can significantly reduce corrosion compared to earlier reactors used to perform hydro-regeneration of spent acidic ionic liquids.

In one embodiment, the segmented reactor is designed and operated to maintain a pressure in the segmented reactor in a range that is optimal for regenerating the acidic ionic liquid. In one embodiment, the pressure in the segmented reactor is greater than 300 kpa. In one embodiment, the segmented reactor additionally comprises a pressure controller than maintains the pressure in the segmented reactor from 50 to 5000 psig (446 to 34600 kpa). Other ranges of pressure in the segmented reactor can be 200 to 4000 psig (1480 to 27700 kpa, or 400 to 3000 psig (2860 to 20800 kpa).

In one embodiment, the segmented reactor additionally comprises a fluid connection between the outlet from which the regenerated acidic ionic liquid flows out of the reactor and an alkylation reactor outlet, wherein an extracted conjunct polymer naphtha produced in the segmented reactor is mixed with an alkylate gasoline made in an alkylation reactor, to make a blended alkylate gasoline.

In one embodiment, the segmented reactor additionally comprises a recycle loop that feeds the regenerated acidic ionic liquid back to a hydrocarbon conversion reactor that produced the spent acidic ionic liquid. Examples of hydrocarbon conversion reactors that can produce spent acidic ionic liquids are those that perform an alkylation, a polymerization, a dimerization, an oligomerization, an acylation, a hydrocracking, a metathesis, a copolymerization, an isomerization, a carbonylation, a hydroformylation, a dehalogenation, a dehydration, a disproportionation, a transalkylation, and combinations thereof.

Hydrogenation Catalysts:

In conventional hydrogenation processes, significant quantities of hydrogenation catalysts are added, along with $H_2$, to the organic compounds to be reduced or saturated in a reactor used for regenerating. The amount of the hydrogenation catalyst that is required to be added in earlier conventional hydrogenation processes depends to a large extent on the metals present in the hydrogenation catalyst, but typically the hydrogenation catalyst is added in amounts greater than 5 wt % of the organic compounds being treated. The amount of the metal that needed to be used in the past for the effective hydrogenation of a spent acidic ionic liquid was added in excess to the concentration of the conjunct polymers present in the spent catalyst. Platinum, palladium, rhodium, and ruthenium can form highly active hydrogenation catalysts, which can operate at lower temperatures and lower pressures of $H_2$ compared to other metals. Non-precious metal hydrogenation catalysts, especially those based on nickel (such as Raney-nickel and Urushibara-nickel) have also been developed as economical alternatives, but they are often slower and require higher temperatures. The Raney-nickel catalyzed hydrogenations also require high pressures.

Conventional hydrogenation catalysts can comprise at least one metal selected from the group consisting of elements from Group 6 and Groups 8 through 10 of the Periodic Table. Hydrogenation catalysts can comprise at least one Group 6 metal and at least one metal selected from Groups 8 through 10 of the Periodic Table. For example, the metal can be selected from the group consisting of nickel (Ni), palladium (Pd), platinum (Pt), cobalt (Co), iron (Fe), chromium (Cr), molybdenum (Mo), tungsten (W), and mixtures thereof. Exemplary mixtures of metals that have been used in hydrogenation catalysts include Ni/Mo/W, Ni/Mo, Ni/W, Co/Mo, Co/W, Co/W/Mo, Ni/Co/W/Mo, and Pt/Pd. Exemplary metal combinations used in hydrogenation catalysts include Ni/Mo/W, Ni/Mo, Ni/W, Co/Mo, Co/W, Co/W/Mo and Ni/Co/W/Mo.

Hydrogenation catalysts can be heterogenous or homogeneous. Heterogenous hydrogenation catalysts are in a different phase from the unsaturated organic compounds to be reduced or saturated. Typical examples of heterogeneous hydrogenation catalysts involve a solid catalyst with the unsaturated organic compounds being either liquids or gases. The unsaturated organic compounds are chemisorbed onto the heterogeneous hydrogenation catalyst, and hydrogen forms surface hydrides from which hydrogen can be transferred to the chemisorbed unsaturated organic compounds. Heterogeneous hydrogenation catalysts can be affected by their supports, i.e. the material upon which the heterogeneous hydrogenation catalyst is bound.

Homogeneous hydrogenation catalysts dissolve in the solvent that contains the unsaturated organic compounds to be reduced or saturated. Illustrative homogeneous hydrogenation catalysts include the rhodium-based compound known as Wilkinson's catalyst and the iridium-based Crabtree's catalyst.

Unlike earlier known processes and reactors used for regenerating spent acidic ionic liquids by hydrogenation, the process and segmented reactor for regenerating a spent acidic ionic liquid described herein is done without the addition of a hydrogenation catalyst. Only the spent acidic ionic liquid is contacted with the hydrogen, and the conjunct polymer is reduced sufficiently to produce a regenerated acidic ionic liquid.

This disclosure provides highly efficient reduction of a conjunct polymer content in a spent acidic ionic liquid by hydrogenating and hydrocracking in the complete absence of a solid hydrogenation catalyst. In the absence of a solid hydrogenation catalyst in the segmented reactor, the conjunct polymer can be hydrocracked to lighter molecules that are fully saturated. The reactor pressure and/or $H_2$ partial pressure of the segmented reactor, and the dissolved hydrogen chloride content in the spent acidic ionic liquid can both be important factors. While we do not want to be bound by theory, it is believed that the acidic functionality to perform the hydrocracking can come from the spent acidic ionic liquid. Upon hydrocracking of the conjunct polymer, olefinic reaction intermediates can be created. The olefinic reaction intermediates can then be hydrogenated by the hydrogen gas that is fed to the segmented reactor. The source of the hydrogenation functionality in the hydrogenation reactor can be related to the specific type of acidic ionic liquid used (e.g., organo-aluminum halide) and the hydrogen halide. Dissolved corrosion metals in the spent acidic ionic liquid can also contribute to the hydrogenation and production of fully saturated light hydrocarbons. The contribution of the dissolved corrosion metals on the hydrogenation and hydrocracking, in some embodiments, may be negligible.

In one embodiment, the hydrogen halide in an offgas from the segmented reactor can be monitored. In one embodiment, a level of dissolved hydrogen halide in the spent ionic liquid catalyst can be adjusted to optimize the hydrogenation and hydrocracking in the segmented reactor. The level of dissolved hydrogen halide can be adjusted by increasing an amount of hydrogen halide or alkyl halide co-catalyst used for the hydrocarbon conversion, by increasing a back pressure in the segmented reactor, or by feeding hydrogen halide or alkyl halide to the segmented reactor during the contacting. Back pressure refers to a pressure opposed to the desired flows of the liquid and/or gas in the segmented reactor. The amount of back pressure can be adjusted by valves, a back-pressure regulator, or other obstructions, and also by adjusting a size of the piping in the outlet, a size of the piping in the gas outlet, or installing and adjusting vents in the segmented reactor.

In one embodiment, no drying or reducing of the spent acidic ionic liquid is done before the contacting in the segmented reactor.

Contacting Conditions:

In one embodiment, the conditions used for the contacting include a temperature less than 400° C. (752° F.). In one embodiment, the temperature is from 100° C. (212° F.) to 350° C. (662° F.).

The conditions used for the contacting include a sufficient mixing in the segmented reactor to contact the spent acidic ionic liquid with the hydrogen to produce the regenerated acidic ionic liquid. The sufficient mixing is achieved in part, predominantly (more than half), or in total, by the functioning of the multiple segments in the segmented reactor as bubble column reactors. The sufficient mixing is done by the bubbling of the gas feed comprising the hydrogen. In addition, the sufficient mixing can be also be done using any equipment in the vessel that provides additional effective mixing, such as agitating, baffling, stirring, shaking, vortexing, whisking or any other methods (or combinations thereof) known to produce the sufficient mixing. Examples of equipment that can be used to provide the effective mixing include baffles, paddles, agitators, stirrers, nozzles, screens, filters, vibrators, vortex mixers, gas injectors, dispersers, and combinations thereof.

The conditions for the contacting include an adequate supply of hydrogen to produce the regenerated acidic ionic liquid. In one embodiment, the contacting occurs in the segmented reactor fed with hydrogen gas and the segmented reactor has a pressure greater than 300 kpa. In one embodiment, the contacting occurs in the segmented reactor under a pressure from 50 to 5000 psig (446 to 34600 kpa).

In one embodiment, hydrogen chloride is formed during the contacting. The hydrogen chloride can be dissolved into the spent acidic ionic liquid. In one embodiment, the acidity of the spent acidic ionic liquid can be modulated by an amount of hydrogen chloride in the segmented reactor. In one embodiment, the amount of the hydrogen chloride in the spent acidic ionic liquid in the segmented reactor is maintained at a level that increases a rate of decrease of the content of the conjunct polymer. For example, a back-pressure regulator can be used to modulate the amount of hydrogen chloride in the segmented reactor.

The regenerated acidic ionic liquid can be produced over a wide range of times, depending on the contacting conditions used. Generally, the contacting time in the segmented reactor is greater than 5 minutes. In one embodiment, the contacting time is from five minutes to 50 hours. In one embodiment, the contacting time is from 5 minutes to 10 hours.

In one embodiment, paraffinic light gases are formed during the contacting. These light gases can be entirely non-olefinic, and may comprise $C_2$-$C_4$ alkanes, such as ethane, propane, i-butane, and n-butane. Other examples of paraffinic light gases include methane, ethane, propane, butane, pentane, and mixtures thereof.

In one embodiment, an extracted conjunct polymer naphtha having between 5 and 30 carbon atoms is produced by the contacting in the segmented reactor. In one embodiment, the extracted conjunct polymer naphtha has a final boiling point less than 246° C. (475° F.), a Bromine Number of 5 or less, and at least 30 wt % naphthenes. In one embodiment, the extracted conjunct polymer naphtha has at least 60 wt % carbon numbers in a range of $C_5$ through $C_{10}$. In one embodiment, the extracted conjunct polymer naphtha can be similar to those produced using solid noble metal hydrogenation catalysts. Extracted conjunct polymer naphthas made by contacting a spent acidic ionic liquid and hydrogen with the addition of a solid noble metal hydrogenation catalyst are disclosed in U.S. Pat. No. 8,704,018. In one embodiment, the extracted conjunct polymer naphtha is mixed with an effluent from an alkylation reactor to make a blended alkylate gasoline.

In one embodiment, no solids are added or formed in the segmented reactor used for the contacting.

Acidic Ionic Liquids:

The most common acidic ionic liquids are those prepared from organic-based cations and inorganic or organic anions. Ionic liquid catalysts are used in a wide variety of reactions, including Friedel-Crafts reactions.

The acidic ionic liquid is composed of at least two components which form a complex. The acidic ionic liquid comprises a first component and a second component. The first component of the acidic ionic liquid will typically comprise a Lewis acid compound selected from components such as Lewis acid compounds of Group 13 metals, including aluminum halides, alkyl aluminum dihalides, gallium halide, and alkyl gallium halide (see the Periodic Table, which defines the elements that are Group 13 metals). Other Lewis acid compounds besides those of Group 13 metals may also be used. In one embodiment the first component is aluminum halide or alkyl aluminum dihalide. For example, aluminum trichloride ($AlCl_3$) may be used as the first component for preparing the ionic liquid catalyst. In one embodiment, the alkyl aluminum dihalides that can be used can have the general formula $Al_2X_4R_2$, where each X represents a halogen, selected for example from chlorine and bromine, each R represents a hydrocarbyl group comprising 1 to 12 atoms of carbon, aromatic or aliphatic, with a branched or a linear chain. Examples of alkyl aluminum dihalides include dichloromethylaluminum, dibromomethylaluminum, dichloroethylaluminum, dibromoethylaluminum, dichloro n-hexylaluminum, dichloroisobutylaluminum, either used separately or combined.

The second component making up the acidic ionic liquid is an organic salt or mixture of salts. These salts may be characterized by the general formula $Q^+A^-$, wherein $Q^+$ is an ammonium, phosphonium, boronium, oxonium, iodonium, or sulfonium cation and $A^-$ is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $Al_2Cl_7^-$, $Al_3Cl_{10}^-$, $GaCl_4^-$, $Ga_2Cl_7^-$, $Ga_3Cl_{10}^-$, $AsF_6^-$, $TaF_6^-$, $CuCl_2^-$, $FeCl_3^-$, $AlBr_4^-$, $Al_2Br_7^-$, $AbBr_{10}^-$, $SO_3CF_3^-$, and 3-sulfurtrioxyphenyl. In one embodiment the second component is selected from those having quaternary ammonium halides containing one or more alkyl moieties having from about 1 to about 9 carbon atoms, such as, for example, trimethylammonium hydrochloride, methyltributylammonium, 1-butyl pyridinium, or alkyl substituted imidazolium halides, such as for example, 1-ethyl-3-methyl-imidazolium chloride.

In one embodiment, the acidic ionic liquid comprises a monovalent cation selected from the group consisting of a pyridinium ion, an imidazolium ion, a pyridazinium ion, a pyrazolium ion, an imidazolinium ion, a imidazolidinium ion, an ammonium ion, a phosphonium ion, and mixtures thereof. Examples of possible cations ($Q^+$) include a butylethylimidazolium cation [beim], a butylmethylimidazolium cation [bmim], butyldimethylimidazolium cation [bmmim], decaethylimidazolium cation [dceim], a decamethylimidazolium cation [dcmim], a diethylimidazolium cation [eeim], dimethylimidazolium cation [mmim], an ethyl-2,4-dimethylimidazolium cation [e-2,4-mmim], an ethyldimethylimidazolium cation [emmim], an ethylimidazolium cation [eim], an ethylmethylimidazolium [emim] cation, an ethylpropylimidazolium cation [epim], an ethoxyethylmethylimidazolium cation [etO-emim], an ethoxydimethylimidazolium cation [etO-mmim], a hexadecylmethylimidazolium cation [hexadmim], a heptylmethylimidazolium cation [hpmim], a hexaethylimidazolium cation [hxeim], a hexamethylimidazolium cation [hxmim], a hexadimethylimidazolium cation [hxmmim], a methoxyethylmethylimidazolium cation [meO-emim], a methoxypropylmethylimidazolium cation [meO-prmim], a methylimidazolium cation [mim], dimethylimidazolium cation [mmim], a methylnonylimidazolium cation [mnim], a methylpropylimidazolium cation [mpim], an octadecylmethylimidazolium cation [octadmim], a hydroxylethylmethylimidazolium cation [OH-emim], a hydroxyloctylmethylimidazolium cation [OH-omim], a hydroxylpropylmethylimidazolium cation [OH-prmim], an octylmethylimidazolium cation [omim], an octyldimethylimidazolium cation [ommim], a phenylethylmethylimidazolium cation [ph-emim], a phenylmethylimidazolium cation [ph-mim], a phenyldimethylimidazolium cation [ph-mmim], a pentylmethylimidazolium cation [pnmim], a propylmethylimidazolium cation [prmim], a 1-butyl-2-methylpyridinium cation[1-b-2-mpy], 1-butyl-3-methylpyridinium cation[1-b-3-mpy], a butylmethylpyridinium [bmpy] cation, a 1-butyl-4-dimethylacetylpyridinium cation [1-b-4-DMApy], a 1-butyl-4-methylpyridinium cation[1-b-4-mpy], a 1-ethyl-2-methylpyridinium cation[1-e-2-mpy], a 1-ethyl-3-methylpyridinium cation[1-e-3-mpy], a 1-ethyl-4-dimethylacetylpyridinium cation[1-e-4-DMApy], a 1-ethyl-4-methylpyridinium cation[1-e-4-mpy], a 1-hexyl-4dimethylacetylpyridinium cation[1-hx-4-DMApy], a 1-hexyl-4-methylpyridinium cation[1-hx-4-mpy], a 1-octyl-3-methylpyridinium cation[1-o-3-mpy], a 1-octyl-4-methylpyridinium cation[1-o-4-mp y], a 1-propyl-3-methylpyridinium cation[1-pr-3-mpy], a 1-propyl-4-methylpyridinium cation[1-pr-4-mpy], a butylpyridinium cation [bpy], an ethylpyridinium cation [epy], a heptylpyridinium cation [hppy], a hexylpyridinium cation [hxpy], a hydroxypropylpyridinium cation [OH-prpy], an octylpyridinium cation [opy], a pentylpyridinium cation [pnpy], a propylpyridinium cation [prpy], a butylmethylpyrrolidinium cation [bmpyr], a butylpyrrolidinium cation [bpyr], a hexylmethylpyrrolidinium cation [hxmpyr], a hexylpyrrolidinium cation [hxpyr], an octylmethylpyrrolidinium cation [ompyr], an octylpyrrolidinium cation [opyr], a propylmethylpyrrolidinium cation [prmpyr], a butylammonium cation [b-N], a tributylammonium cation [bbb-N], a tetrabutylammonium cation [bbbb-N], a butylethyldimethylammonium cation [bemm-N], a butyltrimethylammonium cation [bmmm-N], a N,N,N-trimethylethanolammonium cation [choline], an ethylammonium cation [e-N], a diethylammonium cation [ee-N], a tetraethylammonium cation [eeee-N], a tetraheptylammonium cation [hphphphp-N], a tetrahexylammonium cation [hxhxhxhx-N], a methylammonium cation [m-N], a dimethylammonium cation [mm-N], a tetramethylammonium cation [mmmm-N], an ammonium cation [N], a butyldimethylethanolammonium cation [OHe-bmm-N], a dimethylethanolammonium cation [OHe-mm-N], an ethanolammonium cation [OHe—N], an ethyldimethylethanolammonium cation [OHe-emm-N], a tetrapentylammonium cation [pnpnpnpn-N], a tetrapropylammonium cation [prprprpr-N], a tetrabutylphosphonium cation [bbbb-P], a tributyloctylphosphonium cation [bbbo-P], or combinations thereof.

In one embodiment, the second component is selected from those having quaternary phosphonium halides containing one or more alkyl moieties having from 1 to 12 carbon atoms, such as, for example, trialkyphosphonium hydrochloride, tetraalkylphosphonium chlorides, and methyltrialkyphosphonium halide.

In one embodiment, the acidic ionic liquid comprises an unsubstituted or partly alkylated ammonium ion.

In one embodiment, the acidic ionic liquid is chloroaluminate or a bromoaluminate. In one embodiment the acidic ionic liquid is a quaternary ammonium chloroaluminate ionic liquid having the general formula RR' R" N H+Al$_2$Cl$_7$—, wherein R, R', and R" are alkyl groups containing 1 to 12 carbons. Examples of quaternary ammonium chloroaluminate ionic liquids are an N-alkyl-pyridinium chloroaluminate, an N-alkyl-alkylpyridinium chloroaluminate, a pyridinium hydrogen chloroaluminate, an alkyl pyridinium hydrogen chloroaluminate, a di alkyl-imidazolium chloroaluminate, a tetra-alkyl-ammonium chloroaluminate, a tri-alkyl-ammonium hydrogen chloroaluminate, or a mixture thereof.

The presence of the first component should give the acidic ionic liquid a Lewis or Franklin acidic character. Generally, the greater the mole ratio of the first component to the second component, the greater is the acidity of the acidic ionic liquid.

For example, a typical reaction mixture to prepare n-butyl pyridinium chloroaluminate ionic liquid is shown below:

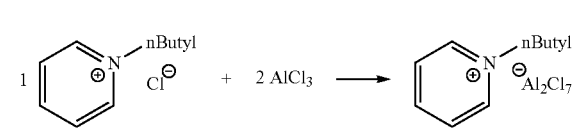

In one embodiment, the acidic ionic liquid is used as a catalyst for a hydrocarbon conversion and the hydrocarbon conversion utilizes a co-catalyst to provide enhanced or improved catalytic activity. A co-catalyst can comprise, for example, anhydrous hydrogen chloride or organic chloride (see, e.g., U.S. Pat. No. 7,495,144 to Elomari, and U.S. Pat. No. 7,531,707 to Harris et al.) When organic chloride is used as the co-catalyst with the acidic ionic liquid, hydrogen chloride may be formed in situ in the apparatus either during the hydrocarbon conversion process or during post-processing of the output of the hydrocarbon conversion. In one embodiment, the hydrocarbon conversion is conducted in the presence of a hydrogen halide, e.g., HCl.

The alkyl halides that may be used include alkyl bromides, alkyl chlorides and alkyl iodides. A variety of alkyl halides may be used, but alkyl halide derivatives of the hydrocarbons that comprise feed streams to the hydrocarbon conversion (e.g., isoparaffins or the olefins for alkylating) can be preferable. Such alkyl halides include but are not limited to isopentyl halides, isobutyl halides, tertiary butyl halides, n-butyl halides, propyl halides and ethyl halides. Alkyl chloride versions of these alkyl halides may be preferred when chloroaluminate ionic liquids are used. Other alkyl chlorides or alkyl halides having from 1 to 8 carbon atoms may be also used. The alkyl halides may be used alone or in combination.

When used, the alkyl halide or hydrogen halide are used in catalytic amounts. In one embodiment, the amounts of the alkyl halides or hydrogen halide should be kept at low concentrations and not exceed the molar concentration of an AlCl$_3$ in the acidic ionic liquid. For example, the amounts of the alkyl halides or hydrogen halide used may range from 0.05 mol % to 100 mol % of the Lewis acid (e.g., AlCl$_3$) in the acidic ionic liquid in order to keep the acidity of the acidic ionic liquid catalyst at the desired performing capacity.

Spent Acidic Ionic Liquid:

Spent acidic ionic liquid can be made by using the acidic ionic liquid to perform the hydrocarbon conversion. Over time, the acidic ionic liquid accumulates impurities and becomes less active and selective for performing the desired hydrocarbon conversion. One of the impurities that accumulates in the acidic ionic liquid can be conjunct polymer. The conjunct polymer deactivates the acidic ionic liquid by weakening the acid strength of the acidic ionic liquid. Complexation of the conjunct polymer with the acidic ionic liquid can deplete the concentration of the Lewis acid in the acidic ionic liquid. As more conjunct polymers accumulate in the acidic ionic liquid the acidic ionic liquid becomes weaker for performing the desired catalysis. In one embodiment, the spent acidic ionic liquid comprises greater than 3 wt % of the conjunct polymer. For example, the spent acidic ionic liquid can have from greater than 3 wt % to 30 wt % conjunct polymer.

The spent acidic ionic liquid can also comprise corrosion metals. The corrosion metals can leach from the metal materials that the acidic ionic liquid contacts and become dissolved in the spent acidic ionic liquid. Examples of metal materials used for vessels and equipment handling acidic ionic liquids are steel, titanium, nickel-copper alloys, and nickel-based super alloys. Examples of some of these metal materials include Inconel® alloys, Incoloy® alloys, Monel® 400 alloy, and Hastelloy® alloys. The compositions of some of these specific alloys are summarized in Table 1. Inconel® and Incoloy® are trademarks of Special Metals Corporation.

TABLE 1

Nickel-Copper Alloy Chemical Composition Ranges (all values in weight percent):

| Alloy | UNS # | Ni | Cu | Fe | Mn | Si | S | C |
|---|---|---|---|---|---|---|---|---|
| Monel® 400 | N04400 | 63.0 min | 28-34 | 2.50 max | 2.0 max | 0.024 max | 0.50 max | 0.30 max |

Monel® is a trademark of Special Metals.

TABLE 2

Nickel Based Super Alloy Elemental Composition Ranges (all values in weight percent):

| Hastelloy® | UNS # | Ni | Cr | Mo | Fe | W | Co |
|---|---|---|---|---|---|---|---|
| C-276 | N10276 | Balance | 14.5-16.5 | 15-17 | 4-7 | 3-4.5 | 2.5 max |
| C-22 | N06022 | Balance | 20-22.5 | 12.5-14.5 | 2-6 | 2.5-3.5 | 2.5 max |
| B2 | N10665 | Balance | 1.0 max | 26-30 | 2.0 max | — | 1.0 max |

| Hastelloy® | UNS # | Mn | C | P | Si | S | V |
|---|---|---|---|---|---|---|---|
| C-276 | N10276 | 1.0 max | 0.01 max | 0.04 max | 0.08 max | 0.03 max | 0.35 max |
| C-22 | N06022 | 0.50 max | 0.01 max | 0.02 max | 0.08 max | 0.02 max | 0.35 max |
| B2 | N10665 | 1.0 max | 0.02 max | 0.04 max | 0.10 max | 0.03 max | — |

Hastelloy® is a trademark of Haynes International, Inc.

In one embodiment, the spent ionic liquid comprises from 100 wppm to 50,000 wppm corrosion metals. In one embodiment, the spent ionic liquid comprises less than 10,000 wppm corrosion metals. In one embodiment, the spent ionic liquid comprises from 10 to 2,500 wppm nickel, wherein the nickel is a corrosion metal.

In one embodiment, the spent acidic ionic liquid catalyst comprises a metal halide. Without being bound by theory, it is possible that a homogeneous metal halide complex forms in situ in the spent acidic ionic liquid catalyst, and that this complex functions as a homogeneous hydrogenation catalyst in the segmented reactor. In one embodiment, the homogeneous metal halide complex comprises nickel. In another embodiment, the homogeneous metal halide complex comprises aluminum and chloride.

Regenerated Acidic Ionic Liquid

After the contacting, the conjunct polymer content in the spent acidic ionic liquid is reduced enough such that the acidic ionic liquid is regenerated. In one embodiment, the conjunct polymer in the regenerated acidic ionic liquid is reduced from 30 wt % to 100 wt % compared to an amount of the conjunct polymer in the spent acidic ionic liquid. In one embodiment, the conjunct polymer in in the regenerated acidic ionic liquid is reduced by at least 50 wt %. In one embodiment the regenerated acidic ionic liquid comprises from 0 to 5 wt % conjunct polymer. In one embodiment, the regenerated acidic ionic liquid comprises less than 1.5 wt % of the conjunct polymer.

Hydrocarbon Conversion Using Acidic Ionic Liquids

Acidic ionic liquids can be used as catalysts for various types of hydrocarbon conversions. Also, the regenerated acidic ionic liquid can also be effective for catalyzing a hydrocarbon conversion in different types of hydrocarbon conversion reactors. Examples of these hydrocarbon conversions include: an alkylation, a polymerization, a dimerization, an oligomerization, an acylation, a hydrocracking, a metathesis, a copolymerization, an isomerization, a carbonylation, a hydroformylation, a dehalogenation, a dehydration, a disproportionation, a transalkylation, and combinations thereof. In one embodiment, the hydrocarbon conversion is alkylation of paraffins with olefins. In another embodiment, the hydrocarbon conversion is alkylation of aromatics. Examples of ionic liquid catalysts and their use for alkylation of paraffins with olefins are taught, for example, in U.S. Pat. Nos. 7,432,408 and 7,432,409, 7,285, 698, and U.S. patent application Ser. No. 12/184,069, filed Jul. 31, 2008. In one embodiment, the acidic ionic liquid is a composite ionic liquid catalyst, wherein the cations come from a hydrohalide of an alkyl-containing amine or pyridine, and the anions are composite coordinate anions coming from two or more metal compounds. In another embodiment the conversion of a hydrocarbon is alkylation of paraffins, alkylation of aromatics, or combinations thereof.

In one embodiment, the feed to the hydrocarbon conversion comprises at least one olefin and at least one isoparaffin. For example the feed can comprise a mixture of at least one mostly linear olefin from $C_2$ to about $C_{30}$. In another embodiment, the feed can comprise at least 50% of a single alpha olefin species. In one embodiment, the olefin feed comprises at least one isomerized olefin.

In one embodiment, the feed to an alkylation reactor comprises one or more $C_4$-$C_7$ isoparaffins and one or more $C_2$-$C_5$ olefins, and the process produces an alkylate gasoline blending component.

In one embodiment, the feed to the hydrocarbon conversion comprises isobutane. Isopentanes, isohexanes, isoheptanes, and other higher isoparaffins up to about $C_{30}$ are also useable in the process and segmented reactor disclosed herein. Mixtures of light isoparaffins can also be used in the present invention. Mixtures such as $C_3$-$C_4$, $C_3$-$C_5$, or $C_4$-$C_5$ isoparaffins can also be used and may be advantaged because of reduced separation costs. The feed to the hydrocarbon conversion can also contain diluents such as normal paraffins. This can be a cost savings by reducing the cost of separating isoparaffins from close boiling paraffins. In one embodiment, the normal paraffins will tend to be unreactive diluents in the hydrocarbon conversion.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

The invention illustratively disclosed herein suitably may be practiced in the absence of any element which is not specifically disclosed herein.

It is claimed:

1. A segmented reactor for regenerating a spent acidic ionic liquid via a hydrogenation reaction and a hydrocracking, comprising: no solid hydrogenation catalyst; a gas inlet on a first side of the segmented reactor for feeding a gas feed comprising a hydrogen; a liquid inlet on an opposing side of the segmented reactor for feeding the spent acidic ionic liquid; partitions along an axis of the segmented reactor that create segments, wherein each segment functions as a bubble column reactor; and an outlet from which a regenerated acidic ionic liquid flows out of the segmented reactor; and wherein a placement of the gas inlet and the liquid inlet create a counter-current flow within the segmented reactor.

2. The segmented reactor of claim 1, wherein the partitions comprise one or more down flow pipes, and orifices.

3. The segmented reactor of claim 1, wherein the partitions comprise one or more gas/liquid contact devices.

4. The segmented reactor of claim 1, wherein the counter-current flow within the segmented reactor provides contacting of an effluent ionic liquid stream within the segmented reactor with a fresh gas feed, which provides more conversion of conjunct polymers in the spent acidic ionic liquid.

5. The segmented reactor of claim 1, wherein the outlet is at a bottom of the segmented reactor.

6. The segmented reactor of claim 1, additionally comprising a gas outlet at a top of the segmented reactor.

7. The segmented reactor of claim 1, wherein the gas inlet is at a bottom of the segmented reactor and the liquid inlet is at a top of the segmented reactor.

8. The segmented reactor of claim 7, wherein the outlet is at a bottom of the segmented reactor, and additionally comprising a gas outlet at a top of the segmented reactor.

9. The segmented reactor of claim 3, wherein the one or more gas/liquid contact devices comprise a valve tray, a bubble cap tray, or a combination thereof.

10. The segmented reactor of claim 1, wherein the liquid inlet is designed to feed a mixture of the spent acidic ionic liquid and a hydrocarbon solvent.

11. The segmented reactor of claim 1, wherein the gas inlet is a perforated plate, a gas sparger, or a porous medium.

12. The segmented reactor of claim 1, wherein a gas feed rate and a column diameter of the segmented reactor are designed to provide a superficial gas velocity of 0.01 cm/s to 5 cm/s.

13. The segmented reactor of claim 1, additionally comprising a particulate filter media having no hydrogenation activity at the top of one or more of the partitions.

14. The segmented reactor of claim 1, wherein the partitions have a layer of one or more solids that create a flow resistance, for gas and liquid flows, within the segmented reactor.

15. The segmented reactor of claim 1, wherein the segmented reactor is designed to provide a mass flow ratio of a liquid feed to the gas feed from 1:1 to 100:1.

16. The segmented reactor of claim 1, additionally comprising a guard bed vessel placed before the segmented reactor that minimizes contaminants going into the segmented reactor.

17. The segmented reactor of claim 1, additionally comprising a back-pressure regulator that modulates an amount of a hydrogen chloride in the segmented reactor.

* * * * *